United States Patent [19]

Osypka

[11] Patent Number: 5,050,602
[45] Date of Patent: Sep. 24, 1991

[54] DEVICE FOR CONNECTING IMPLANTED LEADS WITH CARDIAC PACEMAKERS

[76] Inventor: Peter Osypka, Basler Strasse 109, D-7889 Grenzach-Wyhlen, Fed. Rep. of Germany

[21] Appl. No.: 489,066

[22] Filed: Mar. 2, 1990

[30] Foreign Application Priority Data

Mar. 2, 1989 [DE] Fed. Rep. of Germany ....... 3906598

[51] Int. Cl.⁵ ............................................ A61N 1/372
[52] U.S. Cl. ................................................. 128/419 P
[58] Field of Search ..................................... 128/419 P

[56] References Cited

U.S. PATENT DOCUMENTS

| 3,880,169 | 4/1975 | Starr | 128/418 |
| 4,550,737 | 11/1985 | Osypka | 128/785 |
| 4,633,880 | 1/1987 | Osypka | 128/642 |
| 4,774,951 | 10/1988 | Osypka | 128/419 |

FOREIGN PATENT DOCUMENTS

| 0219608 | 6/1986 | European Pat. Off. . |
| 3035531 | 4/1981 | Fed. Rep. of Germany . |
| 3304506 | 8/1984 | Fed. Rep. of Germany . |

*Primary Examiner*—William E. Kamm
*Assistant Examiner*—Scott M. Getzow
*Attorney, Agent, or Firm*—Peter K. Kontler

[57] ABSTRACT

A fitting which serves to connect the bare proximal end of the conductor in an implanted or implantable lead with a cardiac pacemaker has a deformable tubular socket with a proximal end insertable into a pacemaker and a distal end received in the proximal end of an insulating sleeve the distal end of which contains the tubular liner of an extractible guide serving to facilitate insertion of proximal end of the insulating tube for the conductor. The bare proximal end of the conductor is first slipped onto the tip of a stylet which extends through the axial passage of the socket as well as through the axial hole of the sleeve, and the proximal end of the conductor is then introduced into and through the sleeve and the socket until the front end face of the proximal end of the insulating tube strikes an internal shoulder of the sleeve. The proximal end of the socket is then deformed against the adjacent portion of confined proximal end of the conductor by screws which are mounted in a holder separably surrounding the proximal end of the socket. The stylet props the proximal end of the conductor from within during deformation of the socket. The stylet is then extracted and the holder is detached from the socket.

35 Claims, 3 Drawing Sheets

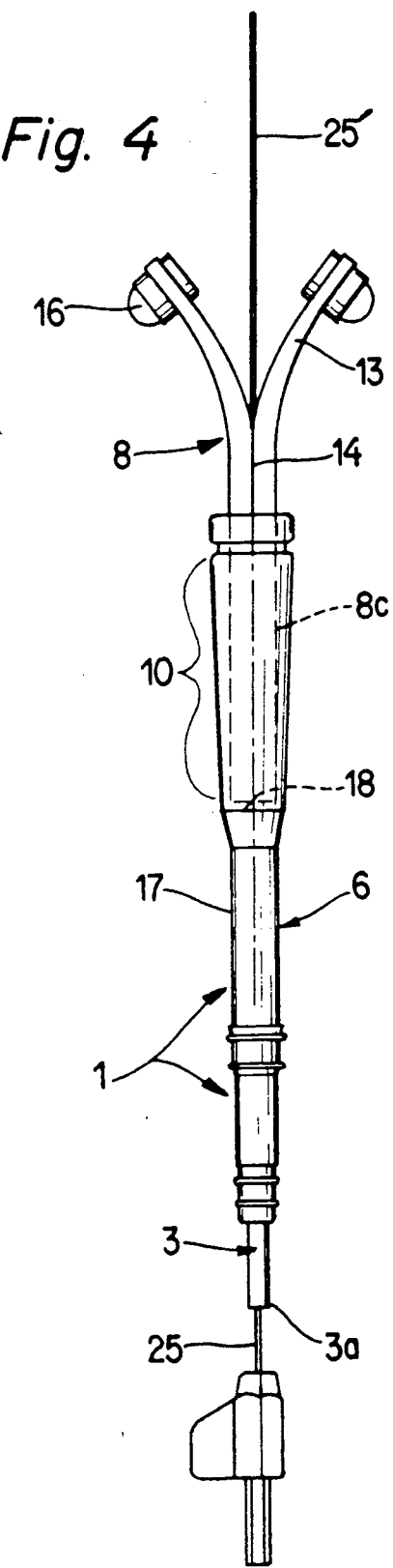
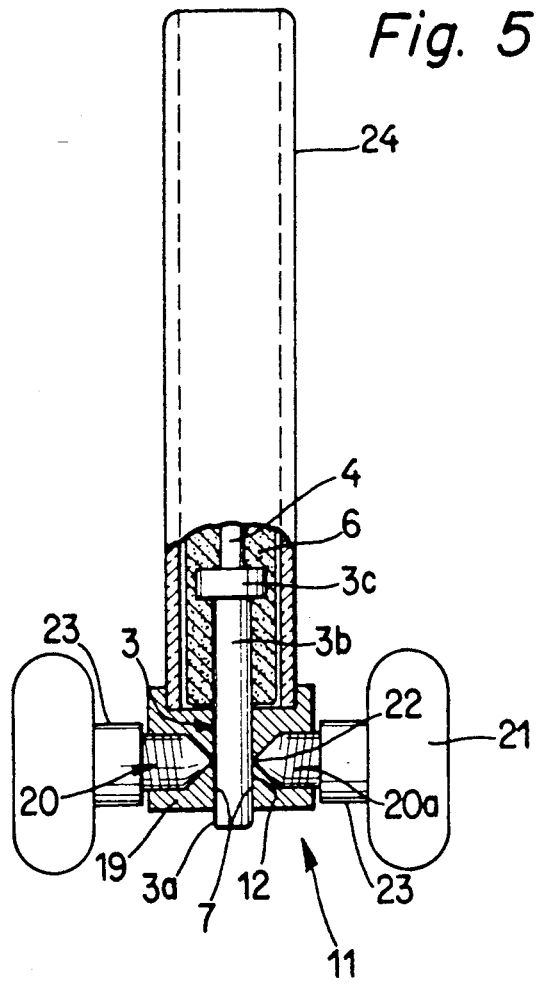

DEVICE FOR CONNECTING IMPLANTED LEADS WITH CARDIAC PACEMAKERS

BACKGROUND OF THE INVENTION

The invention relates to cardiac pacemakers in general, and more particularly to improvements in devices (hereinafter called fittings) which are used to connect implanted or implantable leads with cardiac pacemakers.

Fittings which serve to connect the conductor of an implanted or implantable lead with a cardiac pacemaker normally comprise a terminal (hereinafter called socket) which is connectable with the proximal end of the conductor of the lead and can be plugged into the pacemaker. The socket is normally hollow to receive the proximal end of the conductor, and the socket is coupled with an insulating sleeve which can be coupled to the insulating tube of the lead. The means for electrically connecting the socket with the proximal end of the conductor normally comprises one or more screws which mesh with and extend radially of the socket. The tips of the screws can be driven into the socket to engage the confined proximal end of the conductor. The screw or screws are rotatably mounted in a tubular extension of the socket. A drawback of such proposals is that the space requirements of the socket and of its screw or screws (as seen in the radial direction of the socket) are excessive, i.e., such sockets cannot be plugged into modern pacemakers which have relatively small inlet openings for the sockets.

Commonly owned published German patent application No. 33 04 506 discloses a fitting wherein the socket has an extension for a hollow cylindrical member consisting of convoluted wire and serving to receive the proximal end of the conductor. The hollow cylinder can be deformed into engagement with inserted proximal end of the conductor by a radially disposed screw which is rotatably mounted in the extension of the socket. An advantage of the proposal which is disclosed in the published German patent application is that the proximal end of the conductor is not directly engaged by one or more screws; however, the space requirements of this fitting (in the radial direction of the socket) are still excessive for use with the latest models of pacemakers. Pursuant to international agreements, the diameters of inlet openings of modern cardiac pacemakers are much smaller than in older pacemakers. The diameters should not exceed approximately 3.2 mm which excludes the aforediscussed conventional fittings from use in conjunction with modern pacemakers. On the other hand, it is desirable that a patient who is in need of a new pacemaker receive a modern pacemaker and that such modern pacemaker be connectable with the conductor of an implanted lead.

U.S. Pat. No. 3,880,169 to Starr et al discloses a fitting wherein the part which is connectable to the pacemaker is a pin having an axial blind bore for the proximal end of the conductor. The material surrounding the blind bore is crimped into engagement with the proximal end of the conductor and the latter is further surrounded by a protective wire coil which is introduced into the proximal end of insulating tube of the lead. A standard bayonet mount surrounds the pin and serves to connect the latter with a cardiac pacemaker. The space requirements of this patented fitting are greater than those of the fitting which is disclosed in the commonly owned German patent application No. 33 04 506.

Commonly owned published European patent application No. 0 219 608 discloses an intravenously implantable lead with an electrode provided at the distal end of the conductor and having an external thread for reliable anchoring in the heart. A sleeve is employed to guide the lead during introduction into the vein and such sleeve can be peeled off the introduced lead by destroying its longitudinally extending weakened zones.

Published German patent application No. 30 35 531 of O'Neill discloses a fitting wherein the smaller-diameter distal end of a connecting pin extends into the proximal end of the conductor. The proximal end of the conductor is surrounded by a crimped sleeve which, in turn, is surrounded by the insulating tube of the lead. The insulating tube is surrounded by a bulky connecting sleeve of silicone rubber.

OBJECTS OF THE INVENTION

An object of the invention is to provide a simple, compact and inexpensive fitting which can establish a reliable connection between the conductor of a lead and a pacemaker.

Another object of the invention is to provide a fitting which can connect the conductor of an implanted or implantable lead with a modern or with an antiquated pacemaker.

A further object of the invention is to provide the fitting with novel and improved means for establishing a reliable sealing connection between the part which is connectable to the pacemaker and the insulating tube of the lead.

An additional object of the invention is to provide the fitting with novel and improved means for establishing a reliable mechanical and electrical connection between the conductor of the lead and the part which is to be plugged into the pacemaker.

Still another object of the invention is to provide a fitting which can be installed within a fraction of the time that is required to apply a standard fitting.

A further object of the invention is to provide a fitting which can be readily connected with an insulating tube of silicone and which can be reliably connected with a tubular conductor without subjecting the conductor to any or to excessive deformation.

Another object of the invention is to provide a novel and improved method of manipulating the above outlined fitting.

An additional object of the invention is to provide the fitting with novel and improved means for facilitating coupling of one of its parts with the insulating tube of an implanted or implantable lead.

A further object of the invention is to provide the fitting with novel and improved means for shielding its sensitive parts during storage and/or transport.

Another object of the invention is to provide a fitting which ensures predictable engagement between the conductor of a lead and that part which is to be plugged into a pacemaker, and which ensures predictable insertion of the insulating tube into the complementary part of the fitting.

SUMMARY OF THE INVENTION

The invention is embodied in a fitting which serves to connect a cardiac pacemaker with an implantable or with an already implanted lead wherein the bare proximal end of an elongated conductor extends from the proximal end of an insulating tube surrounding the major portion of the conductor. The improved fitting comprises a tubular socket which is made of a deformable conductive material and has a proximal end connectable with the pacemaker, a distal end and an axial passage for reception of the proximal end of the conductor. The fitting further comprises an insulating sleeve having a proximal end coupled with the distal end of the socket and a distal end for the proximal end of the tube, and means for facilitating introduction of proximal end of the tube into the distal end of the sleeve. The diameter of the passage in the socket is preferably selected in such a way that it at least slightly exceeds the outer diameter of bare proximal end of the conductor to thus facilitate insertion of the bare proximal end into the socket prior to deformation of the socket into conductive engagement with the conductor.

The proximal end of the sleeve preferably surrounds the distal end of the socket, and the sleeve is provided with a through hole having a portion which is surrounded by the distal end of the sleeve and serves to snugly receive the proximal end of the tube.

The aforementioned means for facilitating introduction of the proximal end of the tube into the distal end of the sleeve preferably comprises an at least partially tubular guide which is disposed in the hole at the distal end of the sleeve. That portion of the guide which extends into the hole of the sleeve preferably constitutes an internal liner for a portion of or the entire distal end of the sleeve. The internal surface of the liner is readily slidable onto the proximal end of the tube due to appropriate selection of the material of the liner and/or of the material of the proximal end of the tube and/or due to the finish of internal surface of the liner and/or the finish of the external surface of proximal end of the tube. A second portion of the guide preferably extends from and beyond the distal end of the sleeve to facilitate extraction of the liner from the sleeve upon completed introduction of the bare proximal end of the conductor into the socket and introduction of proximal end of the tube into the liner. The guide can be composed of a plurality of separable or discrete sections each of which has a first part inside and a second part outside of the distal end of the sleeve. The first parts together constitute the liner, and the second parts together constitute the second portion of the guide. When the proximal end of the tube is properly inserted into the sleeve, the first parts of the guide constitute a barrier between the tube and the distal end of the sleeve. At least the liner can be provided with at least one substantially longitudinally extending weakened zone (e.g., with a perforated or grooved zone) to facilitate breakage of the liner along the at least one weakened zone during extraction of the liner from the distal end of the sleeve by grasping and exerting a pull upon the second portion of the guide. The liner can be provided with a plurality of weakened zones, e.g., with two axially parallel weakened zones which are located diametrically opposite each other. At least the liner of the guide can be made of polytetrafluoroethylene, and the second portion of the guide can be provided with at least one handle, e.g., in the form of a protuberance at that end of the second portion which is remote from the distal end of the sleeve.

The socket can be deformed substantially radially inwardly into clamping engagement with the bare proximal end of the conductor in the passage of the socket.

The sleeve can include an intermediate portion which is disposed between its distal and proximal ends and serves to rather snugly receive a portion of the bare proximal end of the conductor.

The fitting is preferably supplied with means for deforming the socket into conductive engagement with the bare proximal end of the conductor in the passage of the socket. Such deforming means preferably includes a holder with an opening (e.g., a through bore or hole) which removably and preferably snugly receives the socket adjacent the proximal end of the sleeve. The arrangement is preferably such that the opening of the holder receives the proximal end of the socket, i.e., that end which is to be connected with the pacemaker upon completed insertion of the bare proximal end of the conductor into the passage of the socket and subsequent deformation of the socket into conductive engagement with the inserted bare proximal end. The deforming means further comprises at least one deforming element which is movably installed in the holder and includes a portion movable against and serving to deform the socket at the opening. The at least one deforming element can constitute or resemble a screw which has an external thread mating with an internal thread of the holder and can be moved substantially radially of the proximal end of the socket in the opening in response to rotation of the screw relative to the holder The head of the screw is located externally of the holder and can be said to constitute a handle which facilitates rotation of the screw by hand or by a suitable implement. The deforming portion of the at least one deforming element is preferably pointed; for example, such pointed portion of the deforming element can resemble or constitute a cone having a tip movable into and from the opening of the holder in response to rotation of the deforming element with reference to the holder It is presently preferred to employ deforming means with a plurality of deforming elements, e.g., with two at least substantially coaxial screws which are disposed at diametrically opposite sides of the proximal end of the socket in the opening of the holder.

The deforming means preferably further comprises means for limiting the extent of penetration of the deforming element or elements into the opening of the holder, i.e., for limiting the extent of deformation of the socket in the opening. Such limiting means can be provided on that portion of each deforming element which is located outside of the holder. If the deforming elements are screws, their shanks can be provided with bosses having shoulders which move against and are thus arrested by the holder in response to rotation of the screws in directions to drive their deforming portions into the opening of the holder. Thus, the shoulders of the bosses cooperate with the holder to arrest the respective screws in predetermined axial positions when the deforming portions of the screws have penetrated into the opening to a predetermined extent.

The holder of the deforming means can be designed to frictionally engage the socket in the opening in undeformed condition of the socket so that the socket and the deforming means constitute a preassembled component which facilitates the task of the physician in charge of connecting the lead with a pacemaker because the socket is already inserted into the opening of the holder but the holder can be readily slipped off the socket when the deforming step is completed, i.e., when the socket is mechanically and electrically connected with the bare proximal end of the conductor.

The holder of the deforming means can carry a shroud which surrounds at least a portion of the sleeve.

The arrangement may be such that the shroud constitutes or includes a pipe which consists, at least in part, of a light-transmitting material (e.g., a plastic material) and surrounds the entire sleeve as long as the proximal end of the socket is received in the opening of the holder.

The sleeve can be provided with an internal abutment for the proximal end of the tube, i.e., the abutment determines the extent of penetration of the proximal end of the tube into the sleeve. The through hole of the sleeve can include a smaller-diameter portion for a portion of the bare proximal end of the conductor and a larger-diameter portion for the proximal end of the tube. The internal abutment can constitute a shoulder between the larger- and smaller-diameter portions of the through hole.

In accordance with a presently preferred embodiment of the fitting, the proximal end of the sleeve surrounds the distal end of the socket and the proximal end of the socket is deformable substantially radially inwardly into mechanical and current-conducting engagement with the bare proximal end of the conductor in the passage of the socket.

The novel features which are considered as characteristic of the invention are set forth in particular in the appended claims. The improved fitting itself, however, both as to its construction and the mode of assembling and using the same, together with additional features and advantages thereof, will be best understood upon perusal of the following detailed description of certain presently preferred specific embodiments with reference to the accompanying drawing.

BRIEF DESCRIPTION OF THE DRAWING

FIG. 4 shows the structure of FIG. 1 but without the lead and with the deforming unit detached from the socket;

FIG. 5 is an enlarged view of the structure of FIG. 1 but with the stylet, the lead and the guide omitted and with the proximal end of the sleeve shown in an axial sectional view.

DESCRIPTION OF PREFERRED EMBODIMENTS

Figure 1:
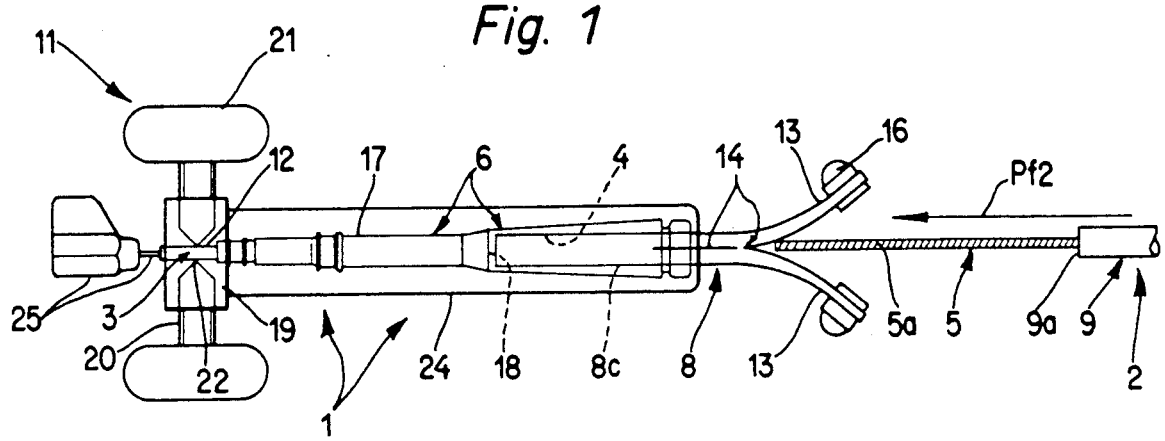
FIG. 1 is a schematic elevational view of a fitting which embodies one form of the invention, the bare proximal end of a conductor forming part of an implanted or implantable lead being shown in the process of penetrating into the sleeve and socket while being guided by a stylet.

The fitting 1 which is shown in the drawing serves to connect a cardiac pacemaker (not shown) with an implanted or implantable lead 2 having a flexible insulating tube 9 which surrounds an elongated electrical conductor 5. The bare proximal end 5a of the conductor 5 extends beyond the proximal end 9a of the tube 9. The manner in which the electrode at the distal end of the conductor 5 can be implanted in the heart of a patient is disclosed, for example, in commonly owned U.S. Pat. Nos. 4,550,737 and 4,633,880. Surgically implantable pacemakers are disclosed in commonly owned U.S Pat. No. 4,774,951. The disclosures of these patents are incorporated herein by reference.

The improved fitting 1 comprises an elongated tubular socket 3 of deformable conductive material. The proximal end 3a (FIGS. 3-6) of the socket 3 is connectable with the pacemaker and the distal end 3b of the socket is coupled to (in the illustrated embodiment inserted into) the proximal end of an elongated insulating sleeve 6. The fitting 1 further comprises an inserter or guide 8 which facilitates introduction of the proximal end 9a of the tube 9 into the through hole 4 of the sleeve 6, and a deforming unit 11 which serves to deform the proximal end 3a of the socket 3 into mechanical current-conducting engagement with the bare proximal end 5a of the conductor 5.

One of the presently preferred uses of the fitting 1 is to establish an electrical connection between an already implanted lead 2 and a pacemaker, e.g., a modern pacemaker which is to replace an antiquated pacemaker. Many modern pacemakers are provided with relatively small inlet openings for reception of conductors, i.e., with inlet openings which are smaller than those of older models. Furthermore, the improved fitting 1 can be used to replace a conventional fitting when the conventional fitting must be removed due to conductor break or for any other reason. Still further, the fitting 1 can be used to connect a freshly implanted lead 2 with a modern pacemaker having a relatively small inlet opening for a conductor which is connected with the electrode of the lead.

Figure 2:
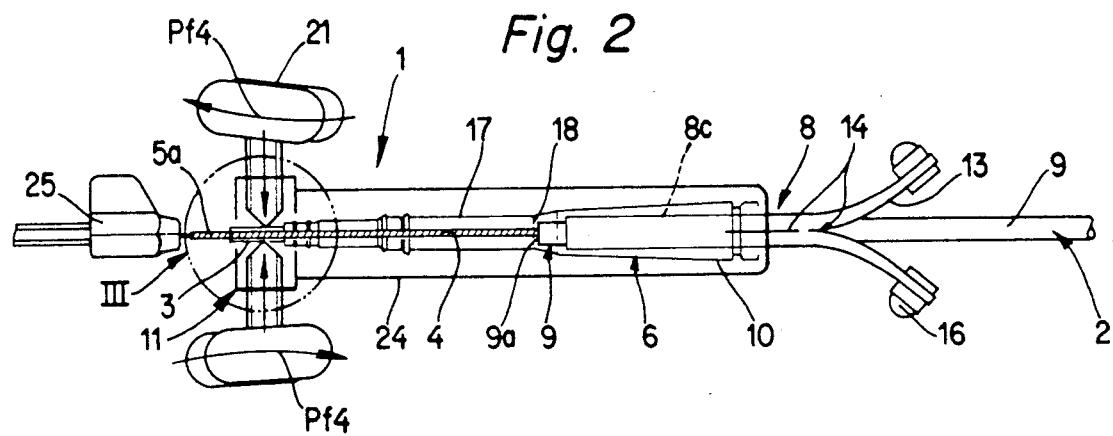
FIG. 2 shows the structure of FIG. 1 but with the proximal end of the conductor and the proximal end of the insulating tube of the lead in fully inserted positions, the deforming elements of the deforming unit being in the process of deforming the proximal end of the socket.
Figure 3:
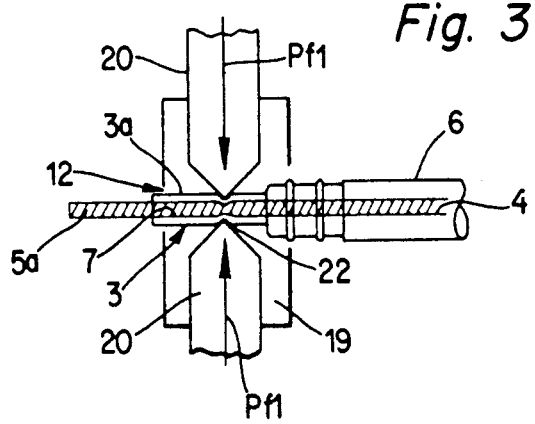
FIG. 3 is an enlarged view of a detail within the phantom-line circle III in FIG. 2.

The outer diameter of the proximal end 3a or of the entire socket 3 is selected in such a way that the proximal end 3a is insertable into the inlet opening of the pacemaker. The through hole 4 of the insulating sleeve 6 has a smaller-diameter portion, a larger-diameter portion and an abutment or stop 18 between the two portions The abutment 18 is an internal shoulder between the two portions of the hole 4 and serves to limit the extent of penetration of proximal end 9a of the tube 9 into the sleeve 6. As can be seen in FIGS. 2 and 3, the bare proximal end 5a of the properly inserted conductor 5 extends through and beyond the smaller-diameter portion of the hole 4 and through and beyond the entire passage 7 of the socket 5 to be severed at the left-hand end of the socket 3 subsequent to radial deformation of the proximal end 3a into mechanical current-conducting engagement with the adjacent confined part of the bare proximal end 5a. The directions in which two mobile deforming elements 20 of the deforming unit 11 are moved relative to their holder 12 in order to deform the proximal end 3a of the socket 3 are indicted by arrows Pf1 (FIG. 3). The diameter of the passage 7 in the socket 3 preferably only slightly exceeds the outer diameter of the normally tubular conductor 5 so that the bare proximal end 5a is snugly received in and is properly guided by the surface surrounding the passage 7 prior to radially inward deformation of the socket 3.

The purpose of the distal end 10 of the sleeve 6 is to sealingly engage the inserted proximal end 9a of the insulating tube 9 irrespective of whether the pacemaker is to be electrically connected with a freshly implanted lead 2 or with a lead which was implanted long prior to utilization of the improved fitting 1 to establish an electrical connection between such implanted lead and a modern pacemaker.

The guide 8 is designed to facilitate insertion of the proximal end portion 9a of the tube 9 into the distal end 10 of the sleeve 6. This is particularly important if the materials of the sleeve 6 and the tube 9 are such that the proximal end 9a could not be readily introduced directly into the distal end 10 of the sleeve. Rapid introduction of the proximal end 9a into the sleeve 6 is highly desirable and can be critical when an already implanted lead is to be connected with a new pacemaker. It is advisable to ensure that the proximal end 9a of the tube 9 be received in the distal end 10 of the sleeve 6 (namely in the larger-diameter portion of the through hole 4) with a minimum of clearance to thus guarantee adequate sealing of the interior of the sleeve and socket 3; such insertion of the proximal end 9a would be difficult or plain impossible, especially within a short interval of time, if the materials of the sleeve 6 and tube 9 are such that the proximal end 9a cannot readily slide along the internal surface of the distal end 10 of the sleeve 6. A tubular (first) portion or liner 8c of the guide 8 is inserted into the distal end 10 of the sleeve 6, either at the manufacturing plant or before the fitting 1 is put to use so that the liner 8c facilitates the task of the surgeon in charge of establishing an electrical connection between the conductor 5 and the pacemaker. To this end, the material of the liner 8c is selected in such a way that it permits rapid and rather effortless insertion of the proximal end 9a of the tube 9. Furthermore, the internal surface of the liner 8c can be finished with a view to facilitate insertion of proximal end 9a of the tube 9 when the fitting 1 is put to use. For example, at least the liner 8c of the guide 8 can be made of polytetrafluoroethylene. As a rule, the material of the sleeve 6 and/or of the insulating tube 5 is silicone.

FIG. 5 shows that the distal end 3b of the socket 3 comprises an annular enlarged portion 3c in the form of a collar which serves to ensure predictable and reliable anchoring of distal end 3b in the proximal end of the sleeve 6. The distal end 3b can be provided with two or more collars or with otherwise configured enlarged portions.

The diameter of that portion of the hole 4 which extends through the distal end 10 of the sleeve 6 matches or only slightly exceeds the outer diameter of proximal end 9a of the tube 9. The arrow Pf2 of FIG. 1 denotes the direction of introduction of bare proximal end 5a of the conductor 5 into and partially beyond the hole 4 of the sleeve 6 and into and partly beyond the passage 7 of the socket 3. This results in introduction of proximal end 9a of the tube 9 into the liner 8c of the guide 8, i.e., indirectly into the distal end 10 of the sleeve 6. The liner 8c is thereupon withdrawn from the distal end 10 in response to exertion of a pull (arrow Pf3 in FIG. 6) upon that (second) portion of the guide 8 which is accessible adjacent the distal end of the sleeve. The free ends 13 of the two parts of the second portion of the guide 8 are provided with handgrip portions or handles in the form of protuberances 16 which can be grasped by fingers or by suitable implements in order to facilitate extraction of the parts 8a, 8b of the liner 8c from the distal end 10 of the sleeve 6 when the introduction of proximal end 9a of the tube 9 into the sleeve is completed. Such extraction of the liner 8c preferably takes place subsequent to establishment of a mechanical current-conducting connection between the socket 3 and the bare proximal end 5a of the conductor 5.

The illustrated liner 8c has two weakened zones 14 which are parallel to the axis of the liner and are disposed diametrically opposite each other. These weakened zones can be formed by providing the liner 8c with grooves and/or perforations so that the guide 8 can be readily and effortlessly divided into two sections each of which includes a first part (8a, 8b) and a second part provided with one of the protuberances 16. The two first parts 8a, 8b of the guide 8 together form the liner 8c, and two second parts together constitute the second portion of the guide 8. The arrows Pf3 in FIG. 6 indicate that the two weakened zones 14 can be destroyed in response to proper selection of the direction of pull upon the protuberances 16 of the second portion of the guide 8.

The weakened zones 14 can be dispensed with if the guide 8 consists of two discrete sections one of which includes the part 8a and one of the protuberances 16 and the other of which includes the part 8b and the other protuberance 16. It is also possible to assemble the guide 8 or an analogous guide of more than two discrete sections or to provide the liner 8c with one, three or more weakened zones 14. All that counts is to ensure that the liner 8c can be readily extracted from the distal end 10 of the sleeve 6. However, it is equally within the purview of the invention to leave at least a portion of the guide 8 on the proximal end 9a of the tube 9. For example, the second portion (including the protuberances 13) of the guide 8 can be separated from the parts 8a, 8b if the liner 8c is to remain in the distal end 10 of the sleeve 6 so that it surrounds and sealingly engages the proximal end 9a of the tube 9 while being maintained in sealing engagement with the surface surrounding that portion of the hole 4 which extends through the distal end 10.

Polytetrafluoroethylene is a presently preferred material of the liner 8c because a tube made of such material can readily slide relative to a tube which is made of silicone, i.e., the proximal end 9a of a silicone tube 9 is readily insertable into a liner 8c which consists of polytetrafluoroethylene. The protuberances 16 at the free ends 13 of the second portion of the guide 8 can be replaced with otherwise configured handgrip portions or handles which facilitate extraction of parts 8a, 8b of the liner 8c from the distal end 10 of the sleeve 6.

The sleeve 6 comprises an intermediate portion 17 which is disposed between the distal end 10 and the proximal end (i.e., between the distal end 10 and the properly inserted distal end 3b). The diameter of the hole 4 in the intermediate portion 17 preferably equals or only slightly exceeds the outer diameter of the conductor 5, i.e., the inserted bare proximal end 5a of the conductor 5 can be snugly received in the intermediate portion 17 of the sleeve 6. The aforementioned abutment (internal shoulder) 18 is disposed between the distal end 10 and the intermediate portion 17 to ensure that the person in charge of inserting the proximal end 9a of the tube 9 into the liner 8c notes when the insertion of the proximal end 9a is completed, i.e., this informs the person in charge that the proximal end 5a of the conductor 5 is in proper axial position for establishment of a mechanical connection with the proximal end 3a of the socket 3. As mentioned above, such mechanical connection (by resorting to the deforming elements 20 of the unit 11) is established prior to extraction of the liner 8c from distal end 10 of the sleeve 6. Such extraction results in separation of the liner 8c into the parts 8a, 8b, i.e., in destruction of the weakened zones 14. All that is necessary to pull the protuberances 16 in the directions which are indicated by the arrows Pf3 of FIG. 6. The sleeve 6 is or can be made of a flexible material.

Another advantage of a guide 8 which is made of polytetrafluoroethylene is that the liner 8c of such guide can have a practically negligible wall thickness so that it occupies a minimum of space in the interior of the distal end 10 of the sleeve 6. A relatively thin liner 8c is desirable on the additional ground that it can be readily destroyed during extraction from the distal end 10, especially if it is provided with one or more weakened zones 14.

The conductor 5 is preferably a space wound coil of the type often employed in leads serving for implantation in human bodies and carrying electrodes for implantation in the heart of a patient. The material of the coil which constitutes the conductor 5 is highly resistant to corrosion and fatigue.

The opening 12 in the holder 19 of the deforming unit 11 is designed to rather snugly receive the proximal end 3a of the socket 3 but without any or without appreciable deformation of the proximal end 3a. Such frictional engagement between the holder 19 and the socket 3 suffices to ensure that the socket and the unit 11 together constitute a preassembled component which is desirable for convenient, rapid and predictable radially inward deformation of selected portions of the proximal end 3a when the introduction of the bare proximal end 5a of the conductor 5 into the passage 7 is completed. The unit 11 is thereupon separated from the deformed proximal end 3a so that the proximal end 3a can be introduced into the aforementioned inlet opening of the pacemaker.

Each deforming element 20 of the illustrated unit 11 is a screw with a shank having external threads 20a (FIG. 5) mating with internal threads of the holder 19. The heads 21 of the screws 20 constitute handles which enable the person in charge to rotate (arrows Pf4 in FIG. 2) the screws in a direction to advance their conical deforming portions 22 into the opening 12, i.e., into deforming engagement with the adjacent portions of the proximal end 3a of the socket 3. When the deforming step is completed, the screws 20 are rotated in opposite directions so that their deforming portions 22 are withdrawn from the opening 12 in order to permit effortless separation of the holder 19 from the proximal end 3a. The two screws 20 are coaxial with each other and are disposed radially of the proximal end 3a. The holder 19 can carry a single screw 20 or three or more screws each of which is preferably designed to deform the adjacent portion of the proximal end 3a radially inwardly toward the axis of the opening 12. An advantage of two mirror symmetrically mounted screws 20 or other suitable deforming elements is that they ensure symmetrical deformation of the proximal end 3a of the socket 3.

The provision of screws 20 with conical deforming portions 22 exhibits the advantage that the resistance to rotation of the screws relative to the holder 19 is not unduly increased when the portions 22 reach and begin to deform the adjacent portions of the proximal end 3a. Were the shanks of the screws 20 provided with flat front end faces (in lieu of the conical portions 22), they would offer much greater resistance to rotation during actual deformation of the socket 3. The heads or handgrip portions 21 can be rotated by hand.

The deforming unit 11 is preferably further provided with means for limiting the extent of deformation of proximal end 3a of the socket 3. Such limiting means comprises two enlarged portions or bosses 23 on the shanks of the screws 20 externally of the holder 19. The front surfaces or shoulders of the bosses 23 engage the adjacent external surfaces of the holder 19 when the portions 22 of the screws 20 penetrate into the opening 12 to a predetermined extent, i.e., when the proximal end 3a has undergone a predetermined deformation which is deemed sufficient to establish a reliable mechanical current-conducting connection between the socket 3 and the bare proximal end 5a of the properly inserted conductor 5. Excessive deformation of proximal end 3a could result in damage to the socket 3 and/or proximal end 5a.

If a mere frictional engagement between the surface surrounding the opening 12 in the holder 19 and the external surface of proximal end 3a of the socket 3 does not suffice to reliably retain the unit 11 on the socket, at least one of the screws 20 is rotated in a direction to move its deforming portion 22 into requisite engagement with the proximal end 3a but without actually or appreciably deforming the proximal end 3a to such an extent that the bare proximal end 5a of the conductor 5 would encounter excessive resistance to penetration into the passage 7. As mentioned above, the provision of a preassembled component including the deforming unit 11 and the socket 3 simplifies the task of the person in charge of establishing an electrical connection between the conductor 5 and the pacemaker.

The holder 19 of the deforming unit 11 can constitute a relatively short cylinder with an axis extending at right angles to the axis of the socket 3. This holder 19 preferably carries a tubular shroud 24 which can be made, at least in part, of light-transmitting plastic material and surrounds at least the proximal end of but preferably the entire sleeve 6 (see FIGS. 1, 2 and 6). The shroud 24 shields and reduces the likelihood of damage to the sleeve 6 during transport and/or storage. Moreover, the shroud 24 can be grasped by hand to facilitate introduction of the proximal end 9a of the tube 9 into the liner 8c of the guide 8. This shroud is removed with the holder 19 when the step of deforming the proximal end 3a of the socket 3 is completed.

The improved fitting 1 is used to establish an electrical connection between a pacemaker and the conductor 5 of an implantable or implanted lead 2 in the following way:

The first step preferably includes introducing an elongated stylet 25 into the proximal end 3a of the socket 3 while such proximal end is surrounded by and is mechanically but separably connected with the holder 19 of the deforming unit 11 (FIG. 1). The proximal end 5a of the conductor 5 is then introduced through the liner 8c of the guide 8 and into the hole 4 of the sleeve 6 (note the arrow Pf2 in FIG. 1) so that it enters into and at least fills the passage 7 of the socket 3. The axial movement of proximal end 5a relative to the socket 3 is terminated when the proximal end 9a of the insulating tube 9 reaches and engages the abutment or shoulder 18 between the larger-diameter and smaller-diameter portions of the hole 4 in the sleeve 6. It goes without saying that the sleeve 6 and the socket 3 can be moved counter to the direction which is indicated by arrow Pf2 in order to be slipped onto the bare proximal end 5a of the conductor 5 and onto the proximal end 9a of the tube 9. The stylet 25 can extend through and well beyond the entire passage 7 to ensure reliable guidance of the tubular proximal end 5a all the way into and through the passage 7. As explained above, the liner 8c of the guide 8 9 into the distal end 10 of the sleeve 6 and all the way into engagement with the abutment or shoulder 18 at the distal end of intermediate portion 17. FIG. 4 shows that the stylet 25 can extend through the entire passage 7 of the socket 3, through the entire hole 4 of the sleeve 6, as well as through and beyond the liner 8c of the guide 8. This ensures that the proximal end 5a of the flexible tubular conductor 5 can be readily slipped onto the protruding tip of the stylet 25 and finds its way into the liner 8c, sleeve 6 and socket 3. The deforming unit 11 is not shown in FIG. 4 in order to illustrate the entire sleeve 6.

The next step involves rotation of one or both screws 20 in order to advance their portions 22 in the directions of arrows Pf1 in FIG. 3, i.e., into the opening 12 of the holder 19, and to deform two mirror symmetrical portions of the proximal end 3a. The deforming step is completed when the bosses 23 of the screws 20 reach and engage the adjacent end faces of the holder 19. The portions 22 of the screws 20 ensure the establishment of reliable form-locking and force-locking mechanical connections between the socket 3 and the conductor 5. The stylet 25 props the proximal end 5a from within during deformation of the proximal end 3a.

The deforming unit 11 can remain connected to the socket 3 while the person in charge exerts a pull upon the protuberances 16 (arrows Pf3 in FIG. 6) in order to destroy the weakened zones 14 of the liner 8c during extraction of this liner from the distal end 10 of the sleeve 6. At such time, the person in charge can grasp the shroud 24 on the deforming unit 11 in order to ensure that the sleeve 6 cannot move during extraction of the liner 8c from the distal end 10. The shroud 24 abuts or is fixed to the holder 19 which, in turn, is mechanically connected to the socket 3 by portions 22 of the screws 20. The distal end 3b of the socket 3 is mechanically coupled with the proximal end of the sleeve 6.

The material of the distal end 10 or the material of the entire sleeve 6 preferably exhibits a certain amount of elasticity so that the distal end 10 can be at least slightly expanded (with or without the liner 8c) in order to further reduce the magnitude of the force which is needed to introduce the proximal end 9a of the tube 9 into the liner 8c. Temporary expansion of the distal end 10 facilitates extraction of the liner 8c upon completed introduction of the proximal end 9a of the tube 9 all the way into engagement with the abutment 18. Expansion of the distal end 10 can be promoted or caused by appropriate chemical treatment of the material of the sleeve 6, and such expansion is only temporary, i.e., the distal end 10 thereupon shrinks to sealingly engage the inserted portion of proximal end 9a upon extraction of the liner 8c. The sealing engagement between the distal end 10 (upon completion of the shrinking step) and the proximal end 9a is sufficiently pronounced to ensure the establishment of a reliable mechanical connection between the lead 2 and the sleeve 6.

The holder 19 of the deforming unit 11 is thereupon detached from the deformed proximal end 3a of the socket 3. Such detachment is preceded by rotation of the screws 20 in directions to withdraw their deforming portions 22 from the opening 12 of the holder 19. The latter is then slipped off the proximal end 3a and entrains the shroud 24, i.e., the sleeve 6 is then exposed. The proximal end 3a remains in form-locking and force-locking engagement with the conductor 5 and is electrically connected thereto.

The stylet 25 is extracted from the proximal end 5a of the conductor 5 prior to separation of the holder 19 from the proximal end 3a. That portion of the proximal end 5a which projects from the proximal end 3a is or can be severed so that the entire proximal end 3a can be inserted into the inlet opening of the pacemaker as soon as the deforming unit 11 is separated from the socket 3.

An important advantage of the improved fitting 1 is that it can be installed within a very short interval of time irrespective of whether the lead 2 is or is not implanted. In addition, the space requirements of the fitting 1 in the radial direction of the sleeve 6 and socket 3 are minimal. Still further, and in spite of such minimal space requirements of the socket 3 and sleeve 6 in the radial direction of the socket, the fitting 1 can establish a highly reliable and long-lasting mechanical and electrical connection between the conductor 5 and the pacemaker by way of the socket 3. The outer diameter of the socket 3 need not exceed 3 mm, i.e., such socket can be readily inserted into the inlet opening of a modern pacemaker.

The proximal end 3a of the socket 3 remains deformed and properly engages the proximal end 5a of the lead 2 without the need for radially extending clamping screws and other bulky parts which are used in presently known fittings.

The proximal end 3a of the socket 3 is receivable in the inlet openings of modern pacemakers, and such socket can be readily connected with the conductor 5 of an implanted lead 2, i.e., in an operating room. The socket 3 need not carry one or more radially extending screws or other deforming elements because such deforming elements (20) are detached from the socket as soon as the deforming step is completed. The diameter of the passage 7 is selected in such a way that it just suffices for rapid and convenient introduction of the proximal end 8 renders it possible to introduce the proximal end 9a of the insulating tube 9 into the distal end 10 of the sleeve 6 with a minimum of effort and with little loss in time. Once the distal end 10 has been caused or permitted to shrink onto the properly inserted proximal end 9a of the tube 9, the outer diameter of the distal end 10 is much less than the outer diameters of insulating sleeves which are used in conventional fittings.

The outer diameters of flexible conductors in implanted leads are sufficiently small to ensure that the proximal ends of such conductors can find room in sockets 3 having an outer diameter not exceeding 3.2 mm as required for insertion into a modern cardiac pacemaker.

Figure 6:
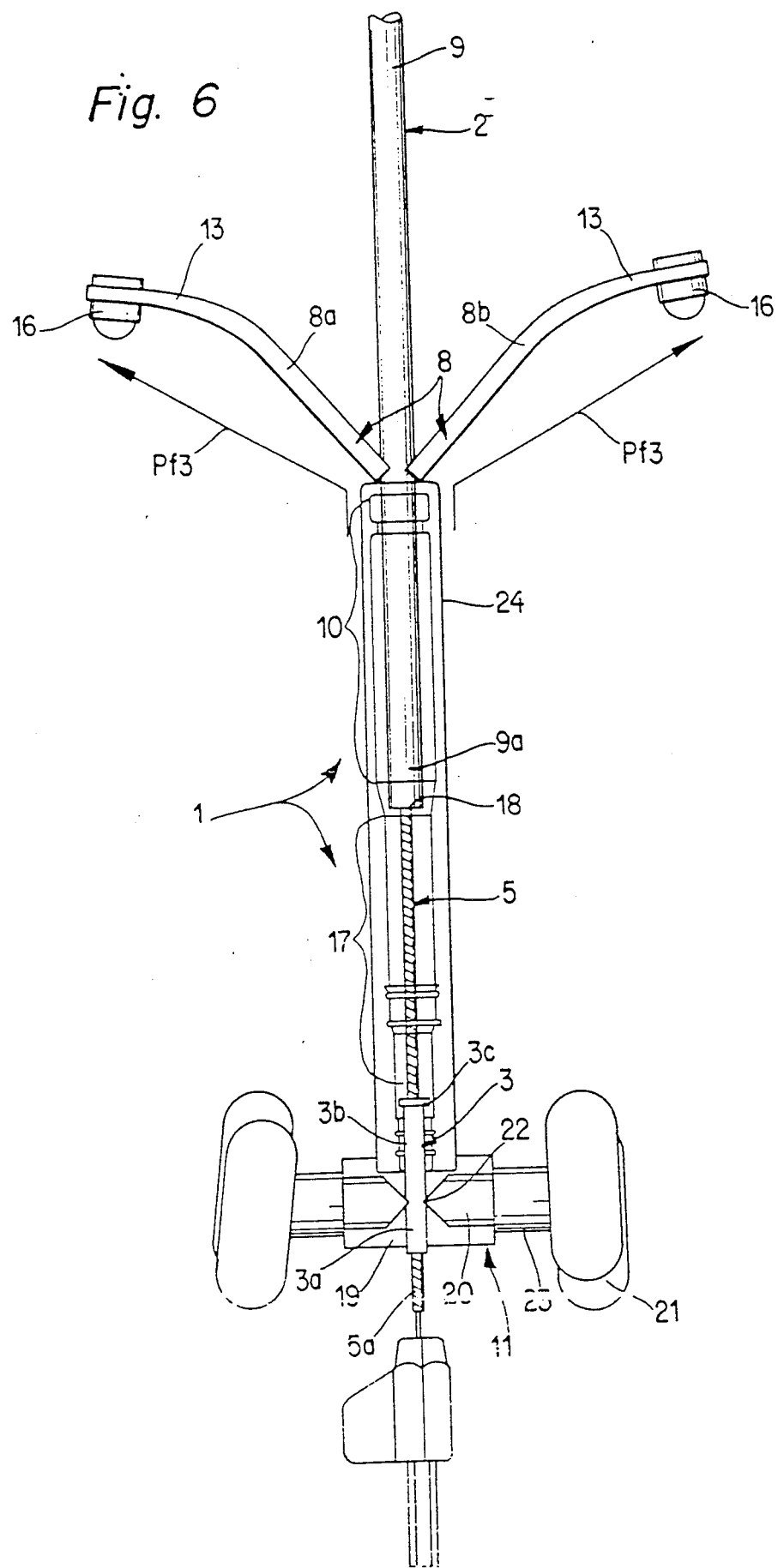
FIG. 6 is an enlarged view of the structure of FIG. 2, showing the guide upon completed extraction of its liner from the distal end of the sleeve.

The guide 8 solves the problem which arises when a first relatively thin insulating member (tube 9) is to be inserted into a second relatively thin insulating member (sleeve 6), especially if the material (e.g., silicone) of these insulating members is such that the first member is not readily slidable in the second member. The liner 8c of the guide 8 acts not unlike a shoe horn in that it permits much more convenient (indirect) insertion of proximal end 9a of the tube 9 into the distal end 10 of the sleeve 6 than if the person in charge were compelled to force the proximal end 9a directly into the distal end 10. Introduction of the proximal end 9a into the liner 8c is rendered even more convenient if the distal end 10 is expanded in the aforediscussed manner. This renders it possible to properly introduce the proximal end 9a into the liner 8c even if the inner diameter of the distal end 10 (in non-expanded condition of the sleeve 6) does not exceed the outer diameter of the proximal end 9a. The compatibility or lack of compatibility of the material of the guide 8 is immaterial since this guide is preferably and normally separated from the sleeve 6 and from the insulating tube 9 when the insertion of proximal end 9a into the distal end 10 is completed; all that counts is to ensure that the dimensions and the material of the guide 8 (and especially of its liner 8c) be selected with a view to facilitate introduction of the proximal end 9a. The stylet 25 guides the proximal end 5a of the conductor 5 during introduction of this proximal end into the passage 7 of the socket 3, and the stylet 25 indirectly guides the proximal end 9a of the tube 9 during introduction into the liner 8c. The feature that the material of the guide 8 is selected with a view to permit convenient insertion of the proximal end 9a into the liner 8c is equally useful during extraction of parts 8a, 8b of the liner 8c from the distal end 10 because the parts 8a, 8b are readily slidable relative to the properly inserted proximal end 9a as well as with reference to the distal end 10. In other words, the force which must be applied to the protuberances 16 in order to extract the parts 8a, 8b from the distal end 10 by pulling the protuberances in directions which are indicated by arrows Pf3 of FIG. 6 is relatively small, and any movement of the sleeve 6 counter to the direction of arrow Pf2 during extraction of parts 8a, 8b from the distal end 10 can be readily opposed by grasping the shroud 24 while the deforming portions 22 of the screws 20 still engage the deformed portions of proximal end 3a of the socket 3. It has been found that, once the distal end 10 has been caused or permitted to shrink and to frictionally engage the proximal end 9a, the mechanical connection between the sleeve 6 and the insulating tube 9 is amply sufficient to withstand all anticipated stresses tending to extract the proximal end 9a from the sleeve.

An advantage of the aforedescribed deforming unit 11 is that it enables the person in charge to deform the proximal end 3a of the socket 3 to an optimum extent. This is in contrast to certain presently known procedures which involve the use of pliers or similar tools. When using such a tool, the person in charge is never certain that the deformation of the socket 3 is not excessive or that the deformation suffices to ensure the establishment of a long-lasting electrical connection between the socket and the conductor 5. Excessive deformation of the proximal end 3a of the socket 3 (i.e., excessive flattening of such proximal end) could prevent insertion of the thus deformed proximal end 3a into a pacemaker.

An advantage of intermediate portion 17 of the insulating sleeve 6 is that this portion receives a length of bare proximal end 5a of the conductor 5, i.e., the proximal end 9a of the tube 9 does not extend all the way to the proximal end of the sleeve 6. This is desirable because the intermediate portion 17 of the sleeve 6 is much more readily flexible than if it were to confine a portion of the tube 9. Such ready flexibility of the sleeve 6 is important because it ensures that the lead 2 is deformable in the region close to the pacemaker. This enables the lead 2 to undergo deformation as a result of movements of the corresponding portion of the body in which the lead is implanted.

The holder 19 of the deforming unit 11 exhibits the advantage that it contributes to predictable deformation of proximal end 3a of the socket 3. This is due to the fact that the surface surrounding the opening 12 in the holder 19 is closely adjacent the external surface of the undeformed proximal end 3a, i.e., the outline of the proximal end 3a changes only in those regions where the proximal end is actually engaged by the deforming portions 22 of the screws 20. The proximal end 3a is deformed only radially inwardly, i.e., it cannot be flattened in its entirety and its maximum radial dimension does not exceed the diameter of the opening 12 so that the deformed proximal end 3a can be readily inserted into the relatively small inlet opening of a modern pacemaker.

The heads 21 of the screws 20 enable the person in charge to select the extent of deformation of the proximal end 3a with a high degree of accuracy. The accuracy of adjustment of the extent of penetration of deforming portions 22 into the opening 12 can be enhanced by appropriate selection of the lead of the screw threads 20a.

As mentioned above, it is presently preferred to employ two screw-shaped deforming elements 20 which are coaxial with each other and are disposed at opposite sides of the proximal end 3a of the socket 3. This enables the person in charge to grasp one of the heads 21 with one hand while simultaneously grasping the other head 21 with the other hand preparatory to rotating the screws 20 in opposite directions, e.g., until the bosses 23 strike the adjacent end faces of the holder 19.

The establishment of a separable connection between the holder 19 of the deforming unit 11 and the proximal end 3a of the socket 3 prior to start of attachment of the conductor 5 to the pacemaker enables the person in charge to concentrate entirely on introduction of proximal end 9a of the tube 9 into the distal end 10 of the sleeve 6 prior to concentrating entirely on the deforming step, i.e , on the establishment of a mechanical and electrical connection between the conductor 5 and the socket 3. As mentioned above, the person in charge can use the holder 19 and the shroud 24 as a convenient handle for manipulation of the fitting 1 during introduction of the proximal end 9a of the tube 9 into the distal end 10 of the sleeve 6, i.e., into the liner 8c of the guide 8. The shroud 24 can be made of a rigid or reasonably rigid material which can stand deformation much more satisfactorily than the very thin sleeve 6 and/or socket 3. Thus, by using the holder 19 and the shroud 24 as a handle, the person in charge need not contact the socket 3 and/or the sleeve 6 during introduction of the proximal end 9a into the liner 8c. Prior to separation of the socket 3 from the holder 19, the shroud 24 can be said to constitute an envelope for the parts 3 and 6 of the improved fitting 1.

It will be noted that not only the guide 8 but also the deforming unit 11 and its shroud 24 perform a host of important and desirable functions in addition to their primary functions, namely convenient introduction of proximal end 9a of the insulating tube 9 into the distal end 10 of the sleeve 6 and radially inward deformation of the proximal end 3a of the socket 3. The connection which is established by the improved fitting 1 is stable and long lasting In addition, the fitting 1 renders it possible to establish a reliable electrical connection between the conductor 5 and the cardiac pacemaker within a very short interval of time irrespective of whether or not the lead 2 is implanted at the time the fitting is being put to use. The space requirements of that portion of the improved fitting 1 which is not confined in the pacemaker are minimal, at least when compared with the space requirements of presently known fittings. The seal between the sleeve 6 and the insulating tube 9 is highly satisfactory and long lasting. This is important because body liquids cannot penetrate into the socket 3 and/or into the pacemaker. The proximal end 3a of the socket 3 can be plugged into the most recent types of pacemakers.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A fitting for connecting a cardiac pacemaker with an implanted or implantable lead wherein a bare proximal end of a conductor extends from a proximal end of an insulating tube, comprising a deformable tubular conductive socket having a proximal end connectable with the pacemaker, a distal end and an axial passage for reception of proximal end of the conductor; an insulating sleeve having a proximal end coupled with the distal end of said socket and a distal end with a hole for the proximal end of the insulating tube; and means for facilitating introduction of the proximal end of the insulating tube into the distal end of said sleeve, comprising a substantially tubular guide disposed in said hole at the distal end of said sleeve, said guide having a first portion which is confined in and constitutes an internal liner for at least a portion of the distal end of said sleeve and a second portion extending form the distal end of said sleeve to facilitate extraction of the first portion from the sleeve upon completed introduction of the bare proximal end of the conductor into said socket and introduction of the proximal end of the tube into said first portion.

2. The fitting of claim 1 for connecting a cardiac pacemaker with a lead wherein the bare proximal end of the conductor has a predetermined outer diameter, wherein said passage has a diameter which at least slightly exceeds said outer diameter to facilitate insertion of the bare proximal end of the conductor into said socket prior to deformation of the socket into conductive engagement with the conductor.

3. The fitting of claim 1, wherein the proximal end of said sleeve surrounds the distal end of said socket and said hold is a through hole having a portion surrounded by the distal end of said sleeve and arranged to snugly receive the proximal end of the tube.

4. The fitting of claim 1, wherein said socket is deformable substantially radially inwardly into clamping engagement with the bare proximal end of the conductor in said passage.

5. The fitting of claim 1, wherein the proximal end of said sleeve surrounds the distal end of said socket and the distal end of said sleeve surrounds a portion of said introduction facilitating means, said sleeve including an intermediate portion disposed between the distal and proximal ends thereof and arranged to snugly receive a portion of the bare proximal end of the conductor.

6. The fitting of claim 1, further comprising means for deforming said socket into conductive engagement with the bare proximal end of the conductor in said passage.

7. The fitting of claim 1, wherein said sleeve has an internal abutment for the proximal end of the insulating tube.

8. The fitting of claim 7, wherein said hold is a through hole including a smaller-diameter portion for the bare proximal end of the conductor and a larger-diameter portion for the proximal end of the insulating tube, said abutment including a shoulder between said portions of the hole.

9. The fitting of claim 1, wherein the proximal end of said sleeve surrounds the distal end of said socket and the proximal end of said socket is deformable substantially radially inwardly into conductive engagement with the bare proximal end of the conductor in said passage.

10. A fitting for connecting a cardiac pacemaker with an implanted or implantable lead wherein a bare proximal end of a conductor extends from a proximal end of an insulating tube, comprising a deformable tubular conductive socket having a proximal end connectable with the pacemaker, a distal end and an axial passage for reception of proximal end of the conductor; an insulating sleeve having a proximal end coupled with the distal end of said socket and a distal end with a hole for the proximal end of the insulating tube; and means for facilitating introduction of the proximal end of the insulating tube into the distal end of said sleeve, comprising a substantially tubular guide disposed in said hole at the distal end of said sleeve, said guide being composed of a plurality of separable sections each having a first part inside and a second part outside of the distal end of said sleeve.

11. The fitting of claim 10, wherein the first parts of said sections are disposed between the distal end of said sleeve and the proximal end of the tube upon insertion of the proximal end of the tube into said sleeve.

12. A fitting for connecting a cardiac pacemaker with an implanted or implantable lead wherein a bare proximal end of a conductor extends from a proximal end of an insulating tube, comprising a deformable tubular conductive socket having a proximal end connectable with the pacemaker, a distal end and an axial passage for reception of proximal end of the conductor; an insulating sleeve having a proximal end coupled with the distal end of said socket and a distal end with a hole for the proximal end of the insulating tube; and means for facilitating introduction of the proximal end of the insulating tube into the distal end of said sleeve, comprising a substantially tubular guide disposed in said hole at the distal end of said sleeve, said guide being composed of a plurality of discrete sections each having a first part inside and a second part outside of the distal end of said sleeve.

13. The fitting of claim 12, wherein the first parts of said sections are disposed between the distal end of said sleeve and the proximal end of the tube upon insertion of the proximal end of the tube into said sleeve.

14. A fitting for connecting a cardiac pacemaker with an implanted or implantable lead wherein a bare proximal end of a conductor extends from a proximal end of an insulating tube, comprising a deformable tubular conductive socket having a proximal end connectable with the pacemaker, a distal end and an axial passage for reception of proximal end of the conductor; an insulating sleeve having a proximal end coupled with the distal end of said socket and a distal end with a hole for the proximal end of the insulating tube; and means for facilitating introduction of the proximal end of the insulating tube into the distal end of said sleeve, comprising a substantially tubular guide disposed in said hole at the distal end of said sleeve, said guide comprising a tubular first portion inside and a second portion outside of the distal end of said sleeve, said first portion having at least one substantially longitudinally extending weakened zone to facilitate breakage of the first portion along such weakened zone during extraction of said first portion from the distal end of said sleeve as a result of the application of a pull upon said second portion.

15. The fitting of claim 14, wherein said first portion has a plurality of weakened zones.

16. The fitting of claim 14, wherein at least the first portion of said guide consists of polytetrafluoroethylene.

17. The fitting of claim 14, wherein the second portion of said guide comprises at least one handle.

18. The fitting of claim 17, wherein said at least one handle includes a protuberance on the second portion of said guide.

19. A fitting for connecting a cardiac pacemaker with an implanted or implantable lead wherein a bare proximal end of a conductor extends from a proximal end of an insulating tube, comprising a deformable tubular conductive socket having a proximal end connectable with the pacemaker, a distal end and an axial passage for reception of proximal end of the conductor; an insulating sleeve having a proximal end coupled with the distal end of said socket and a distal end for the proximal end of the insulating tube; means for facilitating introduction of the proximal end of the insulating tube into the distal end of said sleeve; and means for deforming said socket into conductive engagement with the bare proximal end of the conductor in said passage, said deforming means having an opening removably receiving said socket adjacent the proximal end of said sleeve.

20. The fitting of claim 19, wherein said sleeve has a hole for the proximal end of the tube and said facilitating means comprises a substantially tubular guide disposed in said hole at the distal end of said sleeve.

21. The fitting of claim 20, wherein said guide includes a portion which constitutes an internal liner for at least a portion of the distal end of said sleeve.

22. The fitting of claim 21, wherein said liner has an internal surface which is readily slidable onto the proximal end of the tube.

23. The fitting of claim 19, wherein said deforming means comprises a holder, said opening being provided in said holder and being arranged to removably and snugly receive the proximal end of said socket so that the proximal end of the socket can be withdrawn from said holder prior to connection with the pacemaker.

24. The fitting of claim 23, wherein said deforming means further comprises at least one deforming element movably installed in said holder and including a portion movable against and serving to deform the socket at said opening.

25. The fitting of claim 24, wherein said at least one element is movable substantially radially of the socket in said opening.

26. The fitting of claim 25, wherein said at least one element and said holder have mating threads and said at least one element is rotatable relative to said holder.

27. The fitting of claim 26, wherein said at least one element has a handle externally of said holder.

28. The fitting of claim 26, wherein said portion of said at least one element is pointed.

29. The fitting of claim 28, wherein said portion of said at least one element is conical.

30. The fitting of claim 26, wherein said deforming means comprises two deforming elements disposed substantially diametrically opposite each other with reference to the socket in said opening.

31. The fitting of claim 24, further comprising means for limiting the extent of penetration of said at least one element into said opening.

32. The fitting of claim 31, wherein said at least one element includes a second portion which extends from said holder and constitutes a handle, said limiting means being provided on said second portion of said at least one element and being arranged to engage and to be arrested by said holder in response to penetration of said first named portion of said at least one element into said opening to a predetermined extent.

33. The fitting of claim 24, wherein said deforming means frictionally engages the socket in said opening in undeformed condition of the socket so that the socket and the deforming means constitute a preassembled component.

34. The fitting of claim 24, further comprising a shroud carried by said holder and surrounding at least a portion of said sleeve.

35. The fitting of claim 34, wherein at least a portion of said shroud consists of light-transmitting material and said shroud surrounds the entire sleeve as long as the proximal end of said socket extends into said opening.

* * * * *